US007726306B2

(12) United States Patent
Addington et al.

(10) Patent No.: US 7,726,306 B2
(45) Date of Patent: Jun. 1, 2010

(54) INTRA-ORAL NEBULIZER WITH RAINFALL CHAMBER

(75) Inventors: W. Robert Addington, Melbourne Beach, FL (US); Stuart Miller, Indialantic, FL (US); Mary Briganti, Melbourne, FL (US)

(73) Assignee: Pneumoflex Systems, LLC, Melbourne, FL (US)

(*) Notice: Subject to any disclaimer, the term of this patent is extended or adjusted under 35 U.S.C. 154(b) by 841 days.

(21) Appl. No.: 11/557,993

(22) Filed: Nov. 9, 2006

(65) Prior Publication Data

US 2007/0107725 A1 May 17, 2007

Related U.S. Application Data

(63) Continuation-in-part of application No. 11/431,689, filed on May 10, 2006, which is a continuation-in-part of application No. 10/783,442, filed on Feb. 20, 2004, now abandoned.

(51) Int. Cl.
*A61M 15/00* (2006.01)

(52) U.S. Cl. ..................................................... 128/203.12

(58) Field of Classification Search ............. 128/203.12
See application file for complete search history.

(56) References Cited

U.S. PATENT DOCUMENTS 2,280,050 A 4/1942 Alexander et al. ...... 128/203.11
3,097,645 A * 7/1963 Lester ................... 128/200.21
3,998,226 A 12/1976 Harris ................... 128/203.15
4,333,450 A * 6/1982 Lester ................... 128/200.14
4,792,097 A * 12/1988 Kremer et al. ............. 239/338
RE33,717 E * 10/1991 Svoboda ..................... 239/338
5,312,046 A * 5/1994 Knoch et al. ................ 239/338
5,411,208 A 5/1995 Burgener ....................... 239/8
5,678,563 A 10/1997 Addington et al. .......... 128/716
5,685,291 A 11/1997 Marsh ................... 128/200.15
5,823,187 A 10/1998 Estes et al. ............. 128/204.23
6,004,268 A 12/1999 Addington et al. .......... 600/300
6,029,660 A 2/2000 Calluaud et al. ....... 128/203.12

(Continued)

OTHER PUBLICATIONS

2004 Phillip Kitridge Memorial Lecture entitled, "The Inhalation of Drugs: Advantages and Problems" by Joseph L. Row, printed in the Mar. 2005 issue of Respiratory Care, vol. 50, No. 3.

Cates CJ, Bestall J, Adams N., "Holding Chambers Versus Nebulisers for Inhaled Steroids in Chronic Asthma", The Cochrane Cdatabase of Systematic Reviews 2006, Issue 1, Art No. CD001491.pub2. DOI: 10.1002/14651858.CD001491.pub2.

(Continued)

*Primary Examiner*—Nicholas D Lucchesi
*Assistant Examiner*—Diva Ranade
(74) *Attorney, Agent, or Firm*—Allen, Dyer, Doppelt, Milbrath & Gilchrist, P.A.

(57) ABSTRACT

An improved nebulizer places a venturi in a rainfall chamber and in close proximity to or inside a patient's oral cavity. One or more medicine feed lines feeds the medicine to a location proximate to a venturi. The rainfall chamber contains a sump communicating with the venturi for collecting medication not delivered to the patient and for recycling that medication for delivery to the patient. A medicine receiver may be pre-filled with a standard unit dose of medication.

15 Claims, 19 Drawing Sheets

U.S. PATENT DOCUMENTS

| | | | | |
|---|---|---|---|---|
| 6,044,841 | A | 4/2000 | Verdun et al. | 128/200.18 |
| 6,085,741 | A * | 7/2000 | Becker | 128/200.21 |
| 6,183,423 | B1 | 2/2001 | Gaumond et al. | 600/529 |
| 6,398,728 | B1 | 6/2002 | Bardy | 600/300 |
| 6,411,843 | B1 | 6/2002 | Zarychta | 600/546 |
| 6,655,376 | B2 | 12/2003 | Addington et al. | 128/200.24 |
| 6,735,471 | B2 | 5/2004 | Hill et al. | 607/2 |
| 7,270,123 | B2 * | 9/2007 | Grychowski et al. | 128/200.14 |
| 2001/0050086 | A1 | 12/2001 | Addington et al. | 128/898 |
| 2003/0136399 | A1 | 7/2003 | Foley et al. | 128/200.14 |
| 2004/0206351 | A1 | 10/2004 | McFarland, Jr. | 128/203.12 |
| 2005/0081844 | A1 * | 4/2005 | Grychowski et al. | 128/200.14 |

* cited by examiner

INTRA-ORAL NEBULIZER WITH RAINFALL CHAMBER

CROSS REFERENCE TO RELATED APPLICATION

This application is a continuation-in-part of application Ser. No. 11/431,689, entitled, "Intra-Oral Nebulizer", filed May 10, 2006, by W. Robert Addington, Stuart Miller and Mary W. Briganti (70547), which is a continuation-in-part of application Ser. No. 10/783,442, entitled, "Apparatus For Evaluating A Patient's Laryngeal Cough Reflex And Associated Methods", filed Feb. 20, 2004 now abandoned, by W. Robert Addington and Stuart Miller (70538_UT). Each of these applications is hereby incorporated by reference into this specification in its entirety.

BACKGROUND OF THE INVENTION

1. Field of the Invention

The invention is directed to nebulizers and, more particularly to intra-oral nebulizers.

2. Description of the Prior Art

Inhalation is a very old method of drug delivery. In the twentieth century it became a mainstay of respiratory care and was known as aerosol therapy. Use of inhaled epinephrine for relief of asthma was reported as early as 1929, in England. Dry powder inhalers have been utilized to administer penicillin dust to treat respiratory infections. In 1956, the first metered dosed inhaler was approved for clinical use.

The scientific basis for aerosol therapy developed relatively late, following the 1974 Sugar Loaf conference on the scientific basis of respiratory therapy.

A more complete history of the development of aerosol therapy and the modem nebulizer is described in the 2004 Phillip Kitridge Memorial Lecture entitled, "The Inhalation of Drugs: Advantages and Problems by Joseph L. Row; printed in the March 2005 issue of Respiratory Care, vol. 50, no. 3.

The typically used modem nebulizer is delivered as a kit of seven plastic pieces which are assembled prior to use to provide for delivery of the medication to a patient via inhalation. An exploded view of the seven pieces showing their relationship for assembly is given in FIG. 1. There is a mouthpiece 100 that is force fit onto one end of a T connector 110. Similarly, the other end of the T connector 110 is attached to a flex tube 120, also by force fit. The parts are such that the components can be assembled and disassembled with a simple twisting action. Nevertheless, when engaged and pressed together, the pieces form a substantially airtight seal. The bottom part of the T connector 110 is connected to a cup cover 130. That, too, is connected by pushing the cup cover onto the bottom part of the T connector in such a way that the airtight seal is formed. The cup cover 130 has a screen 135 that screens the material going into the T connector. There is a cup 150 for receiving the medicine to be nebulized. The cup also has a venturi projecting through the bottom.

In a typical use, a vial containing the medication for administration through the nebulizer is opened and poured into the cup 150 where it accumulates at the edges of the rounded bottom of the cup. The venturi is surrounded by a conical plastic piece through which it passes. The shape of the conical piece of the medicine cup 150 matches substantially the shape of the venturi cover 140. Once the medicine is poured into the cup, the venturi cover 140 is placed over the venturi and the filled medicine cup is screwed, using threaded portions on each piece, onto the cup cover 130. In this way, the medicine is held in place ready for administration.

In use, the bottom of the airline feeding the venturi in the medicine cup is attached to an air hose 160, to which is applied to a source of air pressure thus activating airflow through the venturi. By venturi action, the exhaust of the air flow through the small opening of the venturi results in a reduction in pressure on the downstream side of the airflow so that the medicine from the medicine cup is fed under positive pressure up in the interstices between the conical shape of the medicine cup and the venturi cover and is exhausted then through the screen 135 into the bottom of the T connector 110.

A patient is asked to inhale the aerosol mist provided through the cup cover screen into the airflow channel between the mouthpiece 100 and the flex tube 120. As a patient takes the mouthpiece 100 in their mouth, and inhales, air flows through the open end of the flex tube 120, through the T connector 110, picking up the aerosol medication and into the patients' air passages through the mouthpiece 100.

3. Problems of the Prior Art

Table 8 of the Respiratory Care article, referred to above, page 381, lists the characteristics of an ideal aerosol inhaler as follows:

TABLE 8

| |
|---|
| Dose reliability and reproducibility |
| High lung-deposition efficiency (target lung deposition of 100% of nominal dose) |
| Production of the fine particles ≦5 μm diameter, with correspondingly low mass median diameter |
| Simple to use and handle |
| Short treatment time |
| Small size and easy to carry |
| Multiple-dose capability |
| Resistance to bacterial contamination |
| Durable |
| Cost-effective |
| No drug released to ambient-air |
| Efficient (small particle size, high lung deposition) for the specific drug being aerosolized |
| Liked by patients and health care personnel |

The standard nebulizer shown in FIG. 1, fails to achieve a number of these characteristics. Specifically, the nebulizer of FIG. 1 wastes medication during exhalation. Further, the particle size is often too large to reach the bottom of the lungs where the medication may be most needed. There is difficulty in estimating the dose of the drug being given to a patient and there is difficulty in reproducing that dose. There is a possibility of contamination when opening the initially sterile kit, poring medication into the cup, and assembling the pieces for use by a patient. There is also considerable inefficiency in the medication delivery, with much of it being deposited in the throat, rather than in the lungs.

BRIEF DESCRIPTION OF THE INVENTION

The invention is directed to an intra-oral or near intra-oral nebulizer that overcomes the problems of the prior art.

This is achieved in one embodiment by placing the venturi that creates the atomized medication preferably inside the mouth of the patient. Close proximity to the lips of a patient is also an alternative.

The invention will be described in more detail with reference to the following drawings.

DETAILED DESCRIPTION OF THE INVENTION

Figure 1:
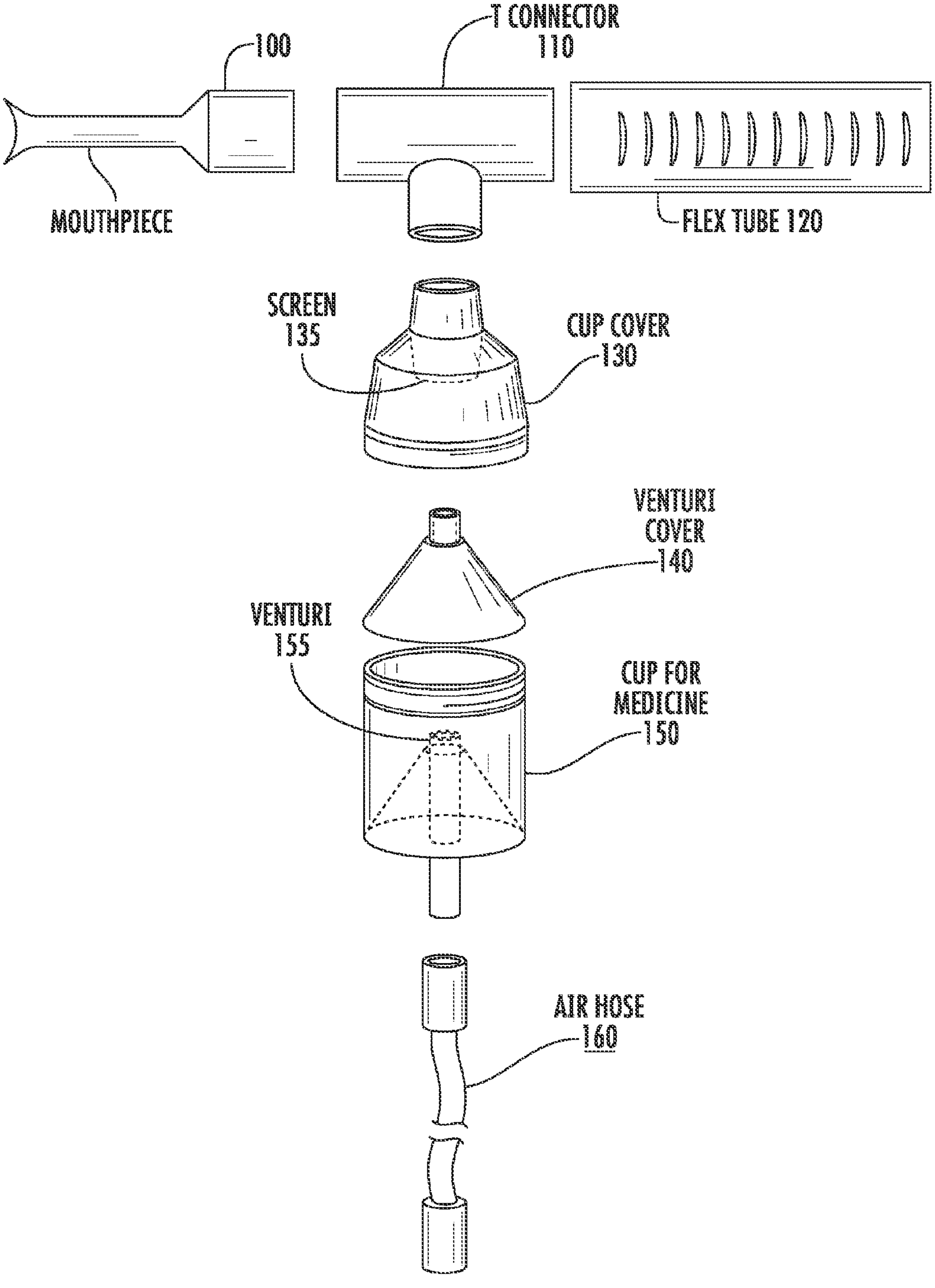
FIG. 1 is an exploded view of a nebulizer kit of the prior art.
Figure 2:
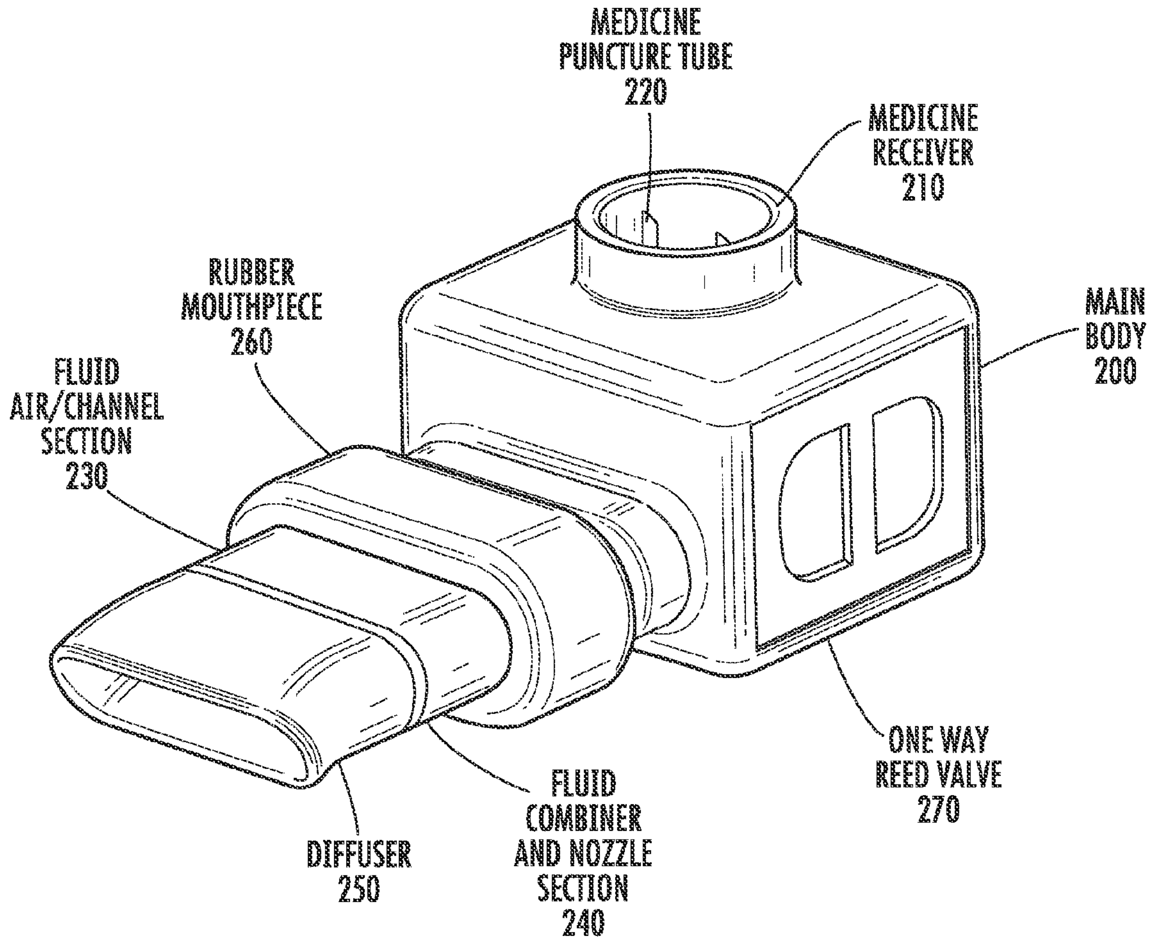
FIG. 2 is a perspective view of an improved nebulizer in accordance with one aspect of the invention.

FIG. 2 is a perspective view of an improved nebulizer in accordance with one aspect of the invention. The nebulizer comprises a main body 200 which has a medicine receiver 210. Extending from the main body is a fluid air channel section 230. The fluid combiner and nozzle section 240 then mates the fluid air channel section 230 with the diffuser 250 as described more hereinafter. A rubber mouthpiece 260, the position of which can be adjusted, surrounds the nebulizer. The medicine receiver 210 is shaped to correspond to the shape of a medication vial or other medication container which, in this embodiment, can be punctured using the medicine puncture tubes 220 which are hollow and which permit the medication then to reach the venturi, discussed more hereinafter, utilizing, in most embodiments, a gravity feed, possibly supplemented with the venturi pressure differential.

Figure 3:
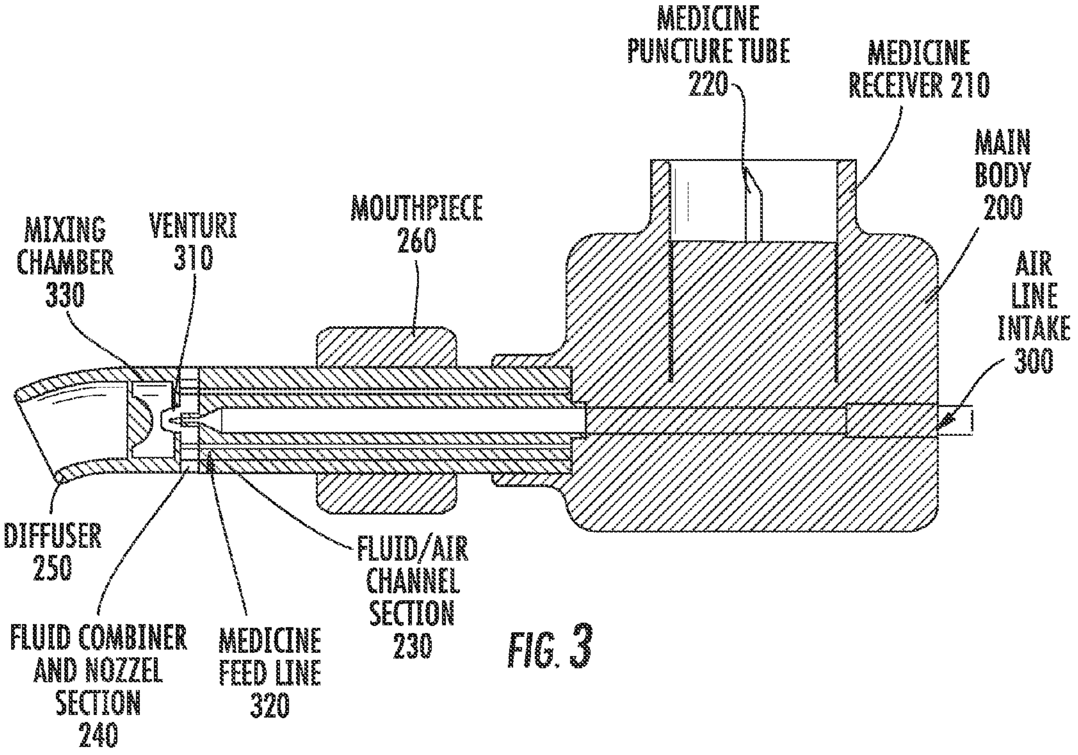
FIG. 3 is a sectional view of the nebulizer of FIG. 2, cut along the centerline of the longitudinal axis.

FIG. 3 is a sectional view of the nebulizer of FIG. 2, cut along the centerline of the longitudinal axis. Here one can see the path of the air from the air line 300 as it goes toward venturi 310. The medicine puncture tube 220 communicates with the medicine feed line 320 allowing the medication to flow from the medication reservoir into the medicine feed line into the mixing chamber 330 where it can be atomized by action of the venturi 310.

Figure 4:
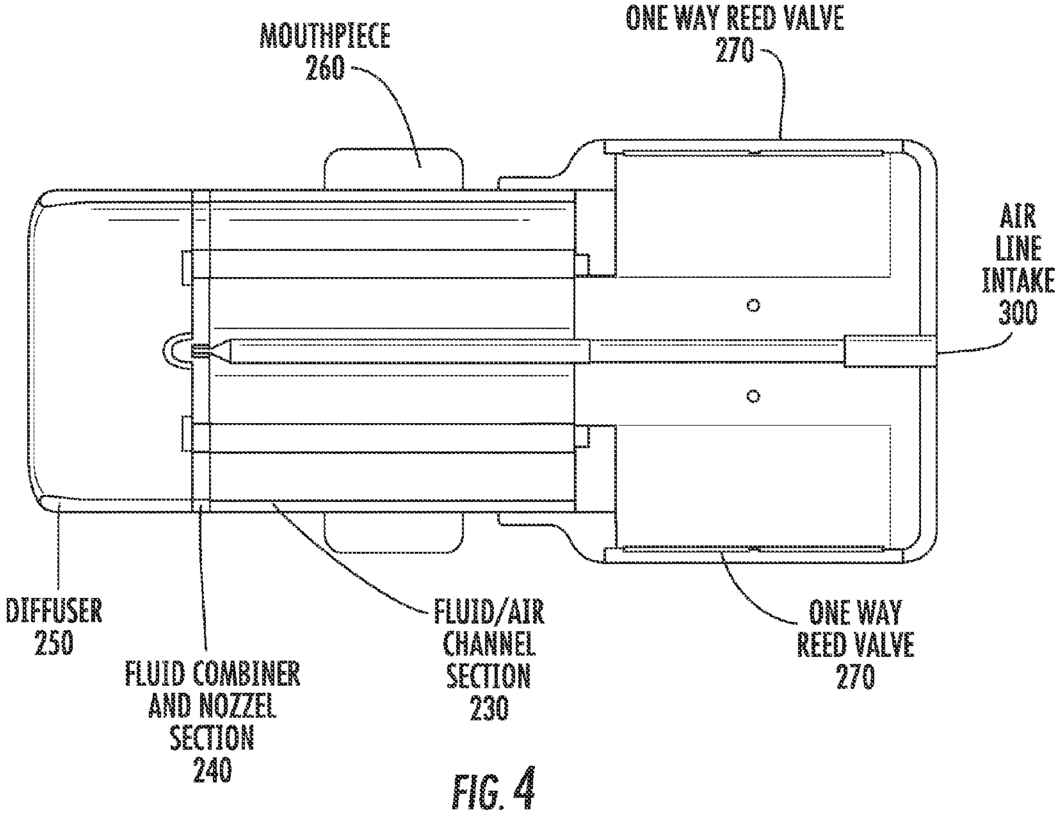
FIG. 4 is a sectional view of the nebulizer of FIG. 2 showing a cut along the transverse axis at the air line.

FIG. 4 is a sectional view of the nebulizer of FIG. 2 showing a cut along the transverse axis at the air line. This view shows the upper half of the nebulizer of FIG. 2 and again shows the air line 300 as it traverses the length of the nebulizer up to the venturi.

Figure 5:
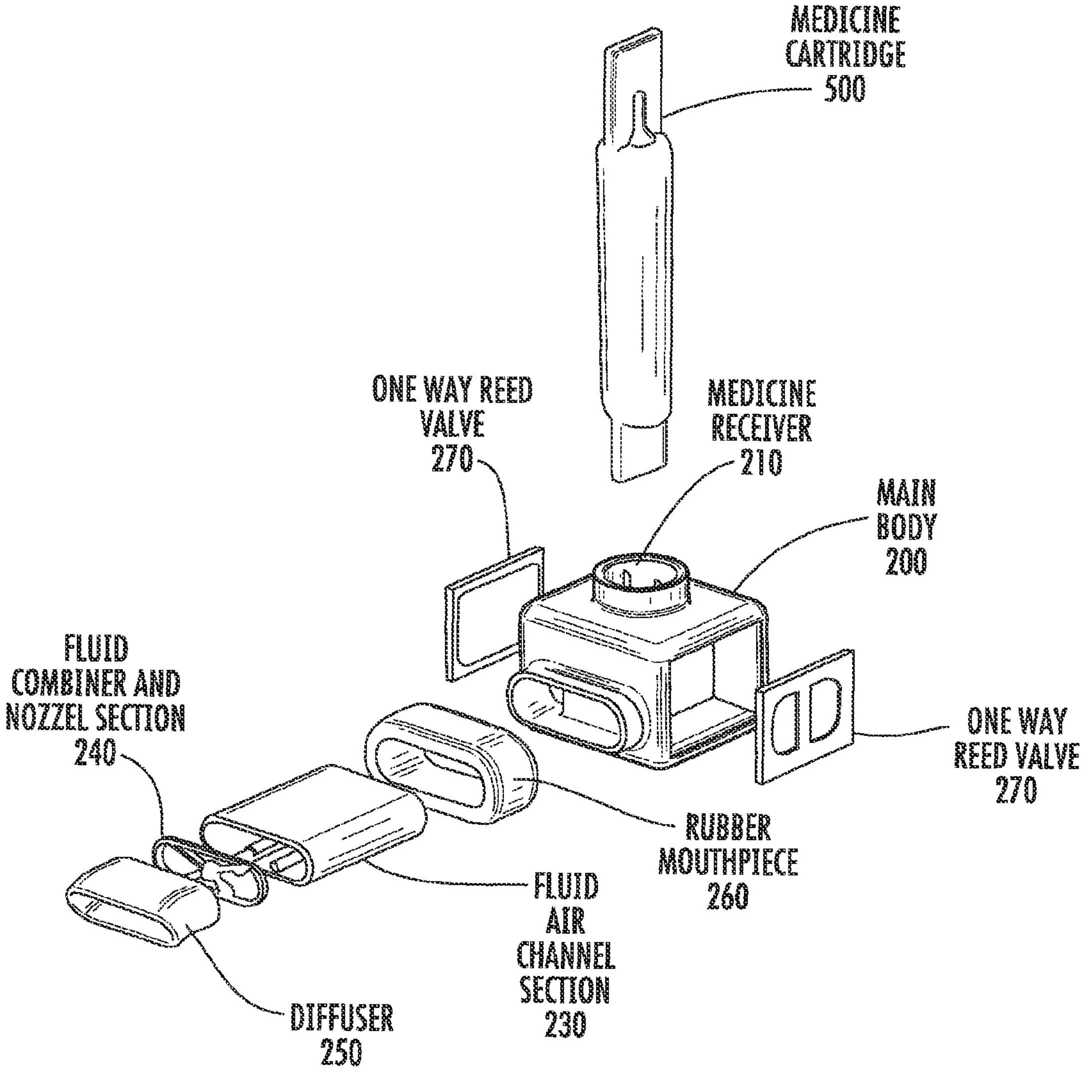
FIG. 5 is an exploded view of the nebulizer of FIG. 2 in accordance with one aspect of the invention.

FIG. 5 is an exploded view of the nebulizer of FIG. 2 in accordance with one aspect of the invention. The nebulizer, as discussed previously, comprises a main body 200. On the main body is a medicine receiver 210 which is shaped to allow the medicine cartridge 500 to fit into the receiver. As the medicine cartridge 500 is inserted in the receiver, the medicine puncture tubes 220 in the medicine receiver 210 will puncture the medicine cartridge 500 allowing the medication to flow into the nebulizer for atomization in the mixing chamber, discussed hereinafter. The medicine puncture tubes 220 can either be a portion of a 22 gauge hollow needle which is press fit into the main body or plastic cast into the main body 200. The far end of the needle communicates with a medicine feed line discussed hereinafter. On either side of the main body 200 are one way reed valves 270, or openings which communicate with air passages in the fluid air channel section 230 to allow inhalation and exhalation by the patient. A fluid air channel section 230 communicates with the main body in such a way as to align with the air passages feeding the inlet and exhaust to openings or one-way reed valves 270. In addition, the fluid air channel section 230 communicates with the air line which is feeding the air to the venturi and with the medicine feed line or lines which bring medicine from the medicine cartridge or reservoir 500. The fluid combiner and nozzle section 240, interfaces between the fluid air channel section 230 in the diffuser 250 as described more in detail hereinafter.

Figure 6:
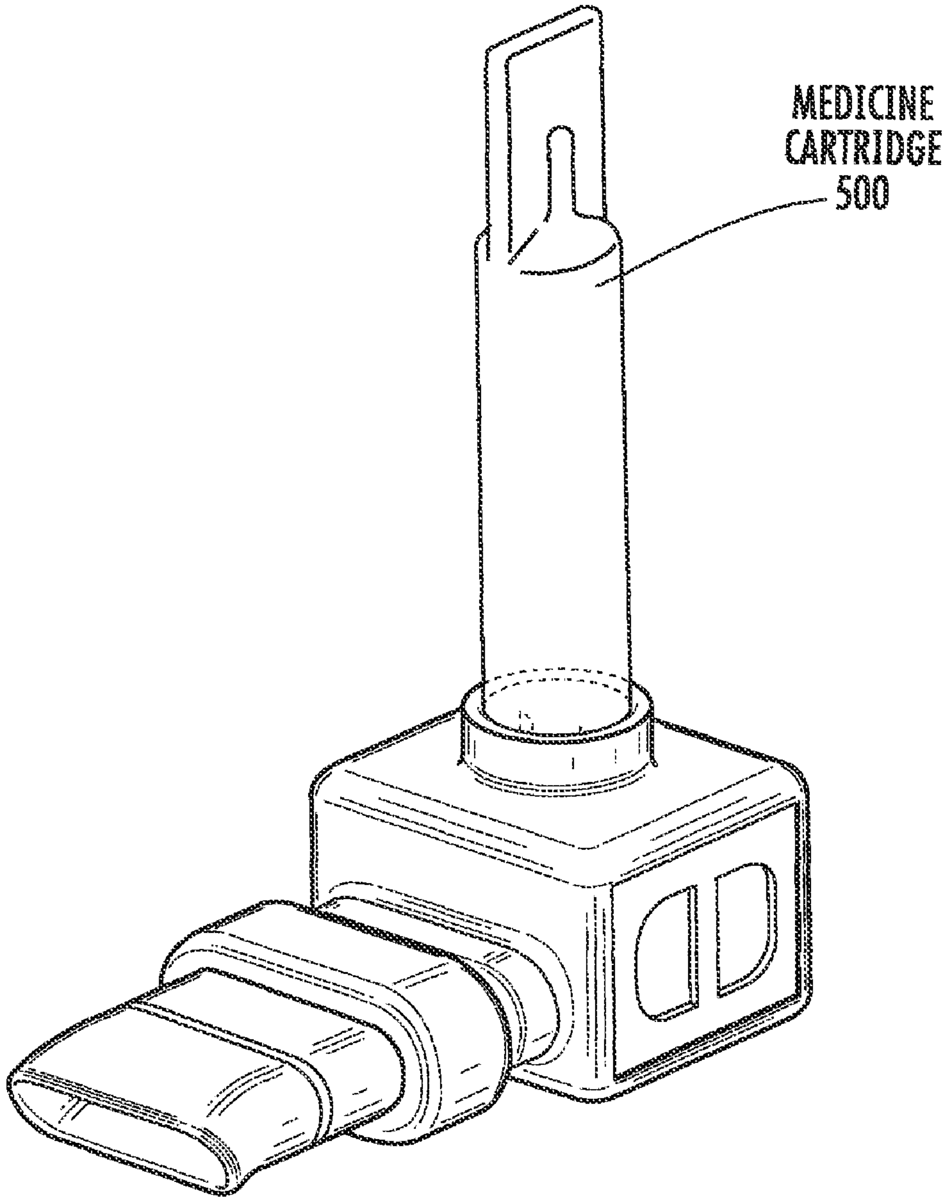
FIG. 6 is an assembled view of the nebulizer of FIG. 2 with a medicine vial in place for use.

FIG. 6 is an assembled view of a nebulizer of FIG. 2 with the medicine vial in place for use.

Figure 7:
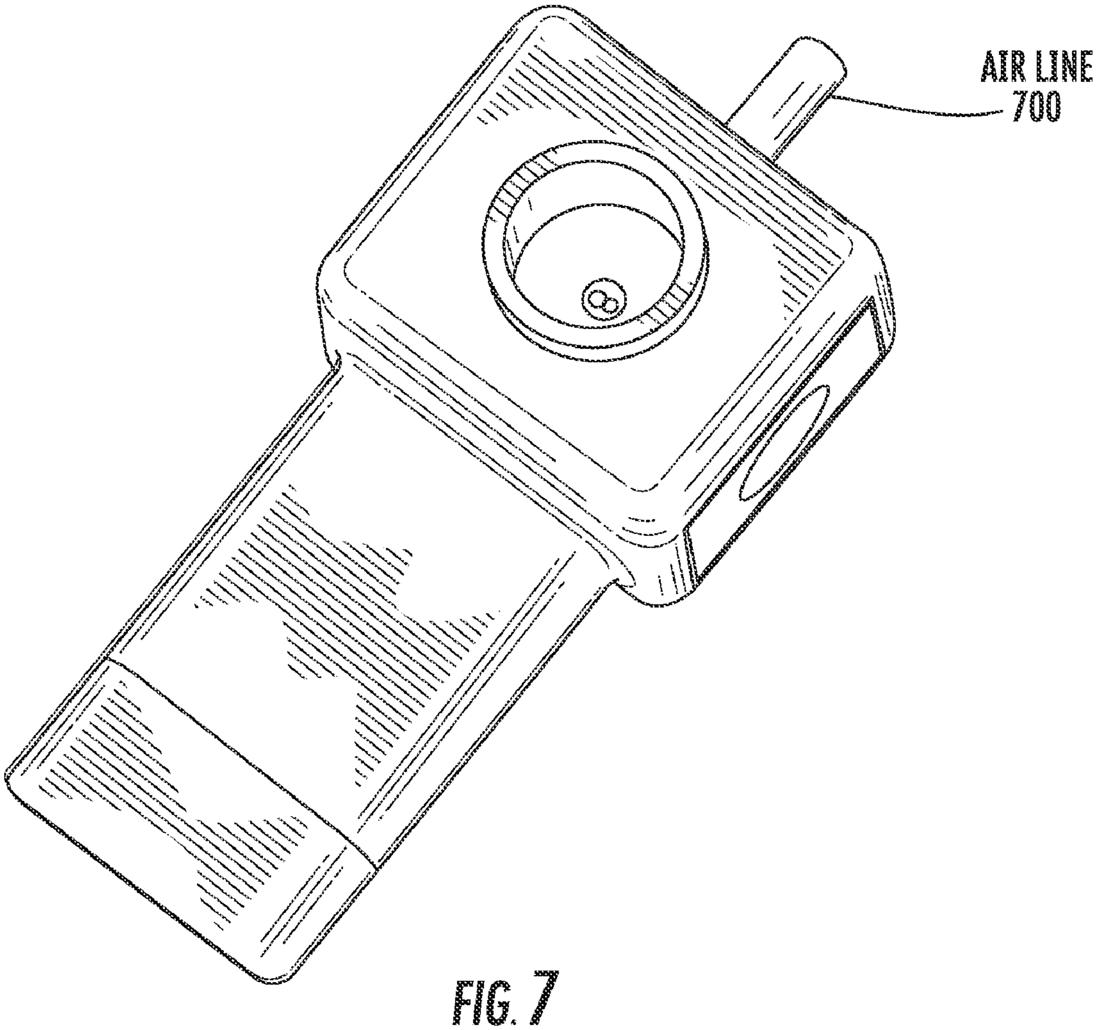
FIG. 7 is a perspective view of a portion of the nebulizer shown in FIG. 2, showing an air line connection.

FIG. 7 is a perspective view of a portion of the nebulizer shown in FIG. 2, showing an air line connection.

Figure 8:
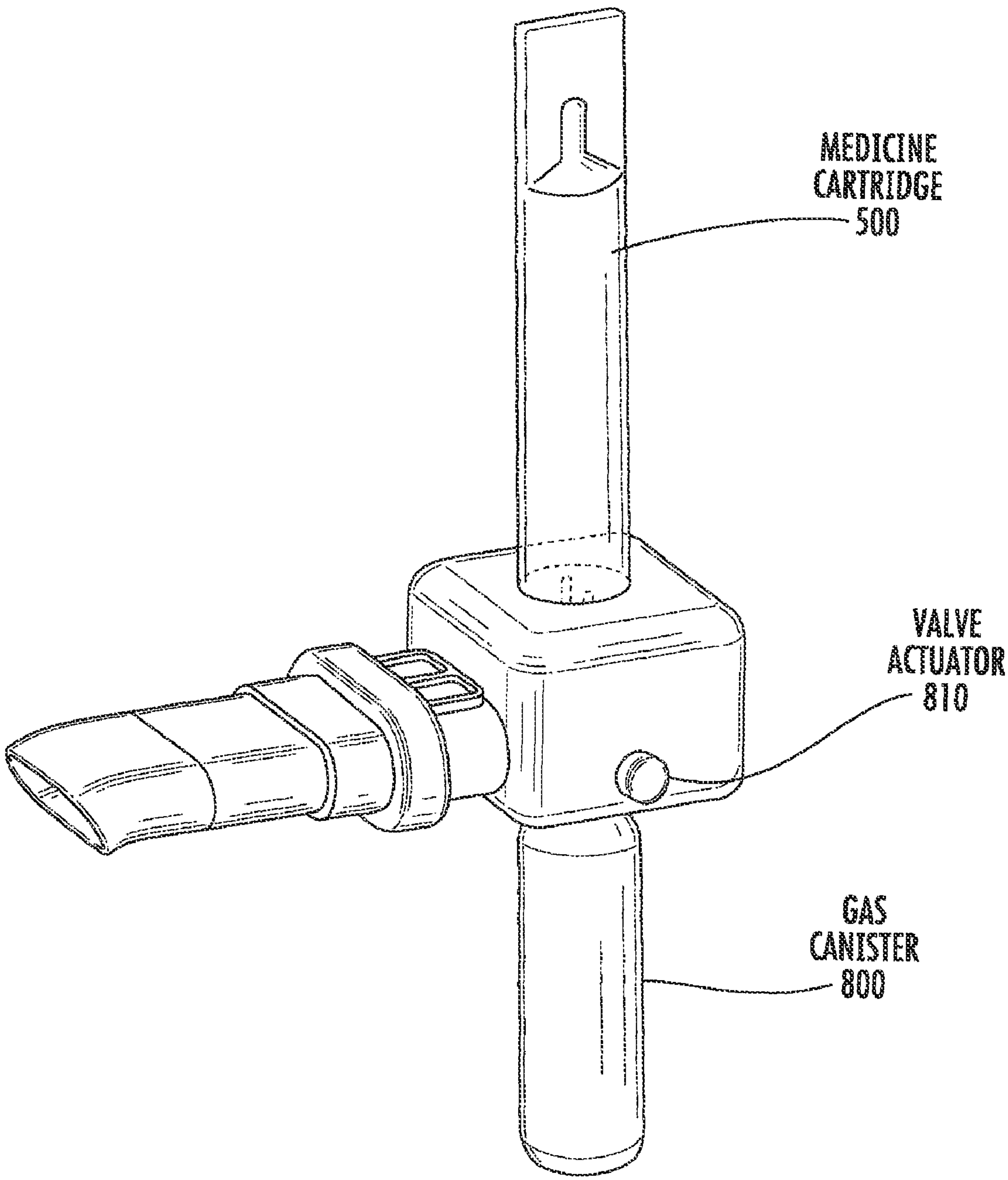
FIG. 8 is an embodiment of a nebulizer that has a pressurized gas canister connected to selectively activate the venturi of the nebulizer.

FIG. 8 is an embodiment of a nebulizer that has a pressurized gas canister connected to selectively activate the venturi of the nebulizer. Replacing an air line, which requires connection to a fixed source of air pressure, such as an oxygen tank or an air tank, is a gas canister 800 which is totally portable. The gas canister connects to the main body of the nebulizer, preferably with a screw on type connection. The passage from the exhaust of the gas canister to the venturi is through a press on release off type of valve which can be selectively activated, using the valve actuator 810 to provide the appropriate level of gas pressure to the venturi for mixing with the medication coming in from medication reservoir 500. In this particular embodiment the air inlet exhaust valves for inhalation and exhalation by the patient, instead of being positioned on each side of the nebulizer, are positioned on the top of the fluid air channel section 230.

Figure 9:
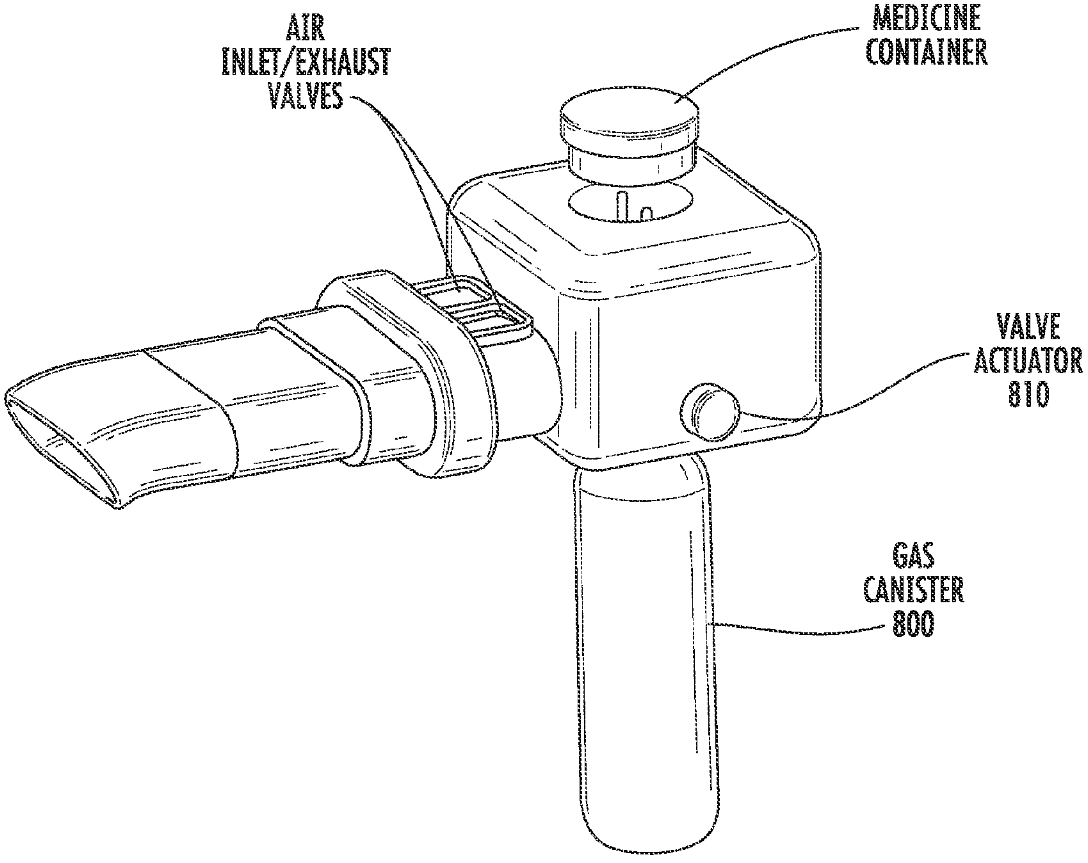
FIG. 9 is a view of the nebulizer of FIG. 8, showing insertion of another type of medicine dispenser.

FIG. 9 is a view of the nebulizer of FIG. 8 showing insertion of another type of medicine container. In this case, the medicine container is shaped to be received by the medicine receiver, previously discussed, in the form of a small button, approximately the size of an antacid tablet, which contains an individual dose of the medication to be utilized. This permits a user to carry with him or her a number of such individual dose containers, optionally packed in a roll, which can be placed into the medicine receiver 210 to dispense the unit dose of medication for the particular patient utilizing the nebulizer. With the medicine in place, a patient can place the distal end of the nebulizer in his mouth, sealing his lips around the rubber mouthpiece 260 and synchronize inhalation with the activation of the valve actuator 810 which then activates the flow of gas from the pressurized gas container 800 through the venturi and the mixing chamber where the medicine from the medicine container is atomized by the action of the venturi and the diffuser plate as described more hereinafter.

Figure 10:
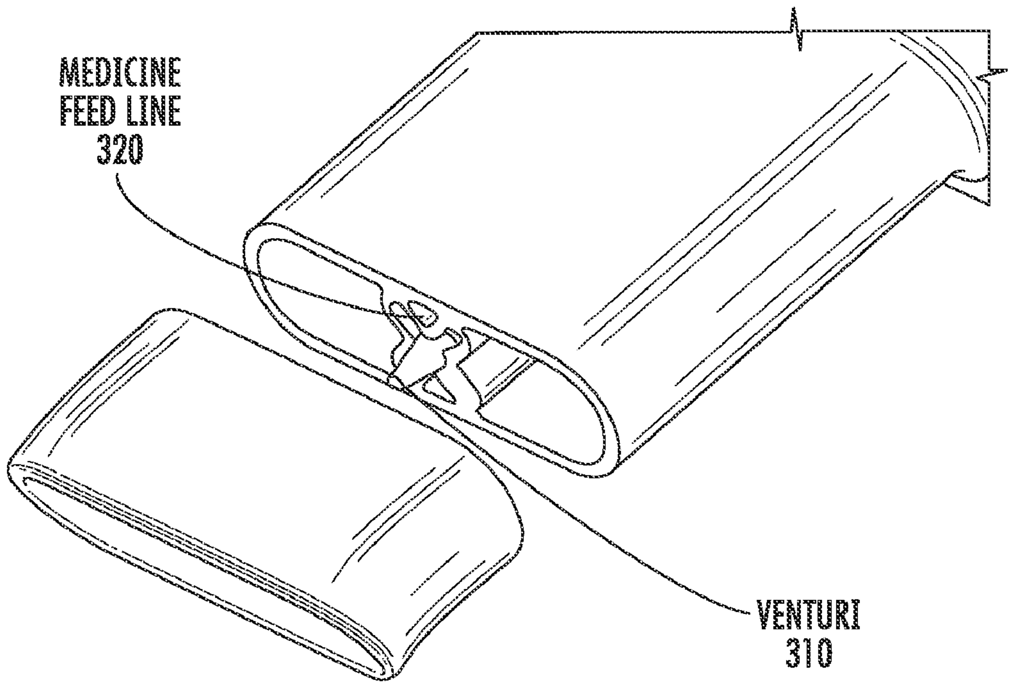
FIG. 10 is a perspective view of the open end of the fluid/air channel section of the nebulizer which interfaces with a fluid combiner and nozzle section and the distal diffuser end piece.

FIG. 10 is a perspective view of the open end of the fluid/air channel section of the nebulizer which interfaces with a fluid combiner and nozzle section and the distal diffuser end piece. As one can see in FIG. 10, the venturi 310 protrudes slightly beyond the end of the main body 200 into a mixing chamber to be shown hereinafter. Proximal to the venturi 310 is a medicine feed line 320.

Figure 11:
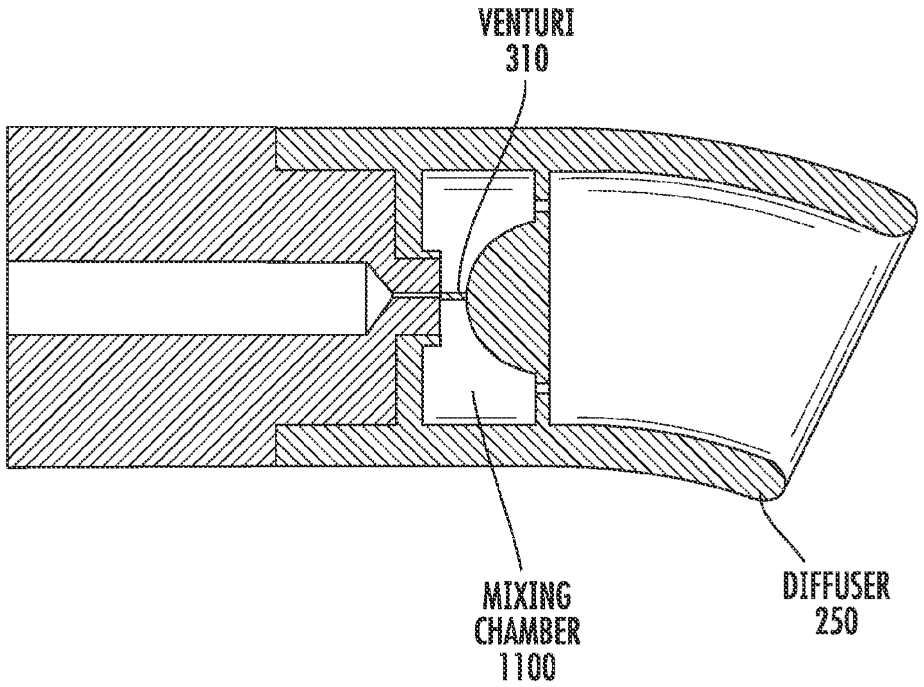
FIG. 11 shows a detailed side sectional view of the venturi, the mixing chamber and a diffuser.

FIG. 11 shows a detailed side sectional view of the venturi, the mixing chamber and a diffuser. The venturi 310 extends into the mixing chamber 1100. The flow of air from the venturi is applied to a spherical diffuser element causing the medication entering the mixing chamber as shown hereinafter to be atomized by the action of the venturi flow.

Figure 12:
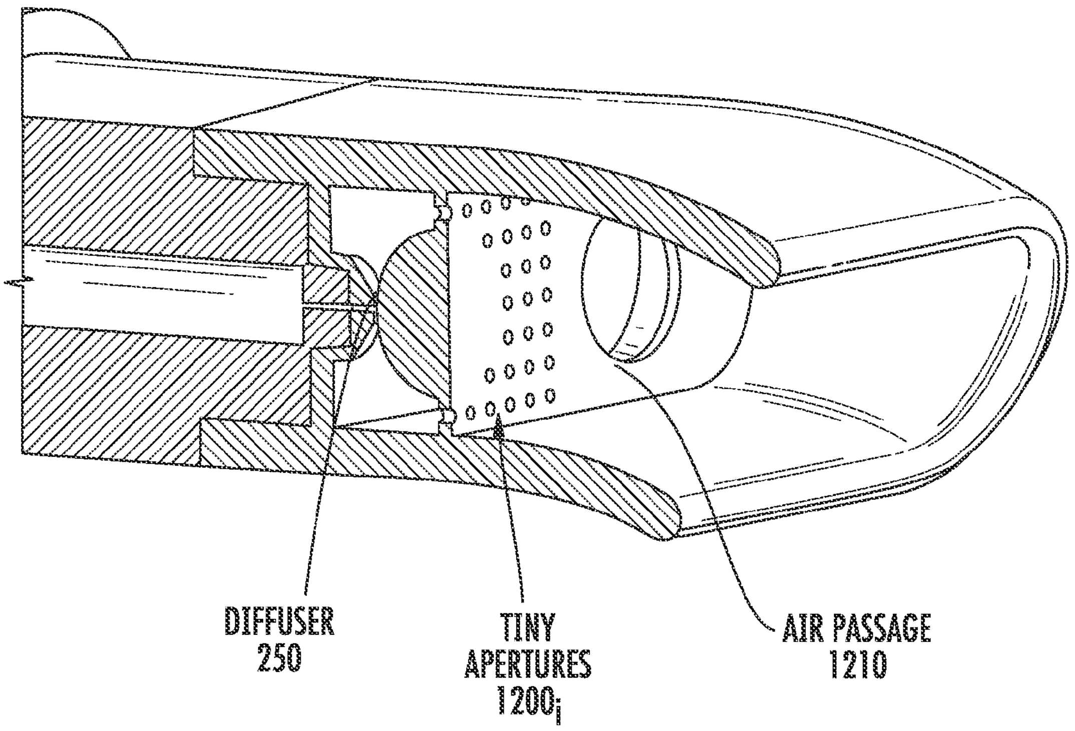
FIG. 12 shows a detailed perspective view of the venturi, mixing chamber and diffuser shown in FIG. 11.

FIG. 12 shows a detailed perspective view of the venturi, mixing chamber and diffuser shown in FIG. 11. In this sectional view, one can see a plurality of tiny apertures $\mathbf{1200}_i$ through which droplets atomized in the mixing chamber by action of the venturi can pass, ensuring some maximum size of the droplets into the area through which the patient inhales and exhales. Since this is a cross section view, only one air passage 1210 is shown. However, there is a corresponding airflow aperture located symmetrically about the cut line. The one-way valves 270 are constructed so that the patient can inhale and exhale through one of the appropriate air passages 1210.

Figure 13:
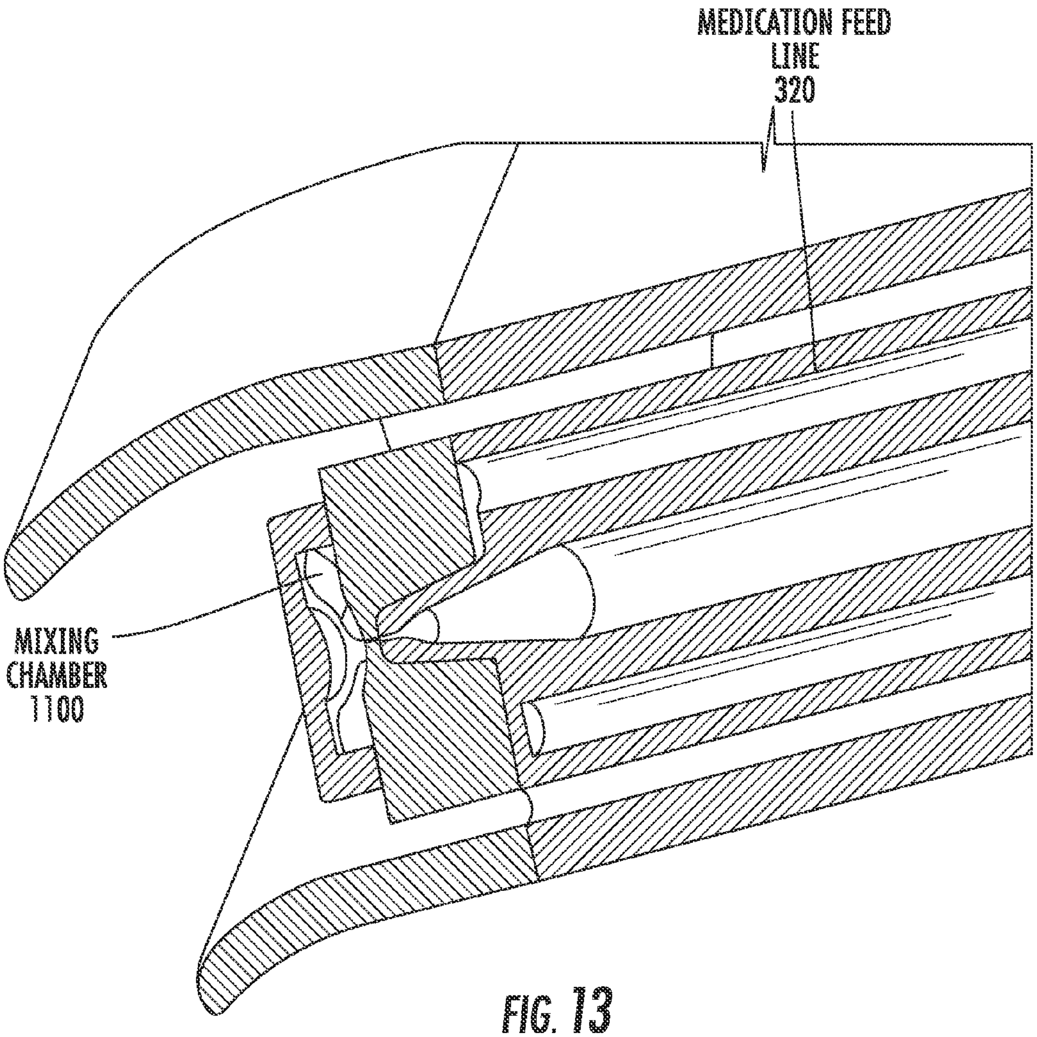
FIG. 13 shows one form of fluid feed from the medicine reservoir to the venturi and mixing chamber.

FIG. 13 shows one form of fluid feed from the medicine reservoir to the venturi and mixing chamber. In this particular embodiment, the medicine from the medicine feed line, which in this embodiment runs parallel to the air line feeding the venturi, ends at the fluid combiner and nozzle section 240. That piece fits over the nozzle, but is designed to allow flow of medication from the medicine feed line down into the proximity of the end of the venturi, exhausting in close proximity to the exhaust point of the venturi itself. The venturi action is such that the high speed flow of the air as it exits the venturi tip results in a considerably decreased pressure vis a vis the surrounding air pressure, which allows a partial vacuum to form which causes the medicine from the medicine feed line to enter into the mixing chamber by virtue of not only gravity feed, but of the pressure differential which results from the venturi action. The turbulence of the venturi feed interacting with the diffuser in close proximity with the medicine fed from the medicine feed line, results in atomization of the medicine in the mixing chamber.

Figure 14:
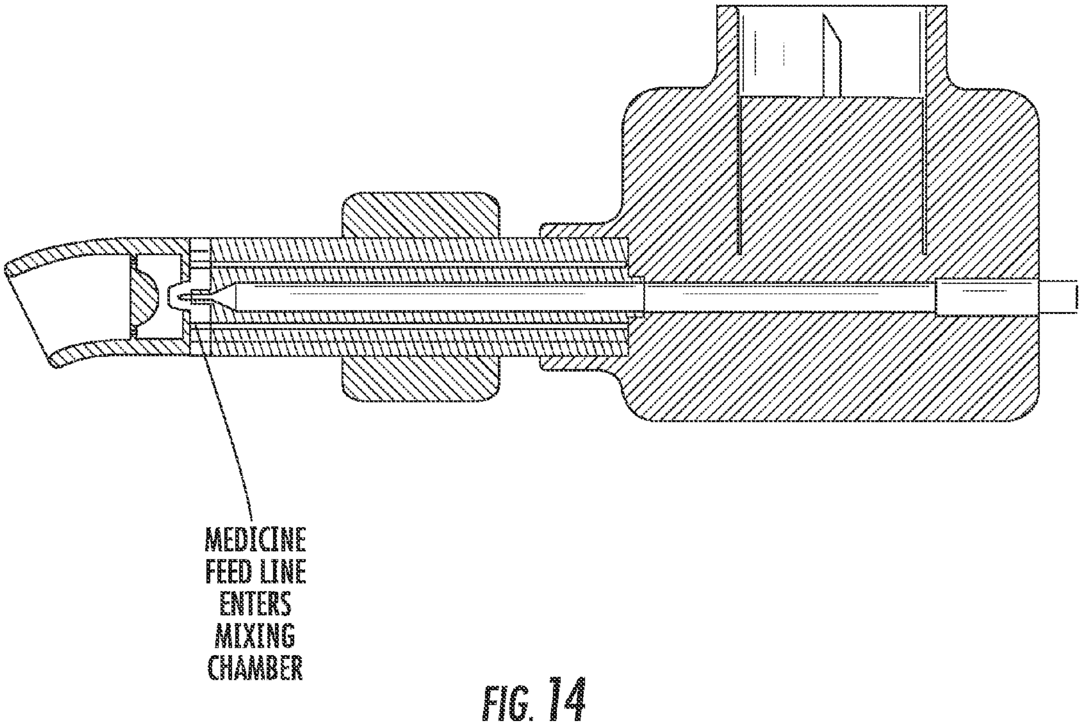
FIG. 14 shows an alternative form of fluid feed from the medicine reservoir to the mixing chamber.

FIG. 14 shows an alternative form of fluid feed from the medicine reservoir to the mixing chamber. In this case, the medicine feed line enters the mixing chamber at a distance somewhat removed from the tip of the venturi. Nevertheless, the action of the venturi and the fuser in the mixing chamber is sufficient to atomize the medication for delivery to the patient.

Figure 15:
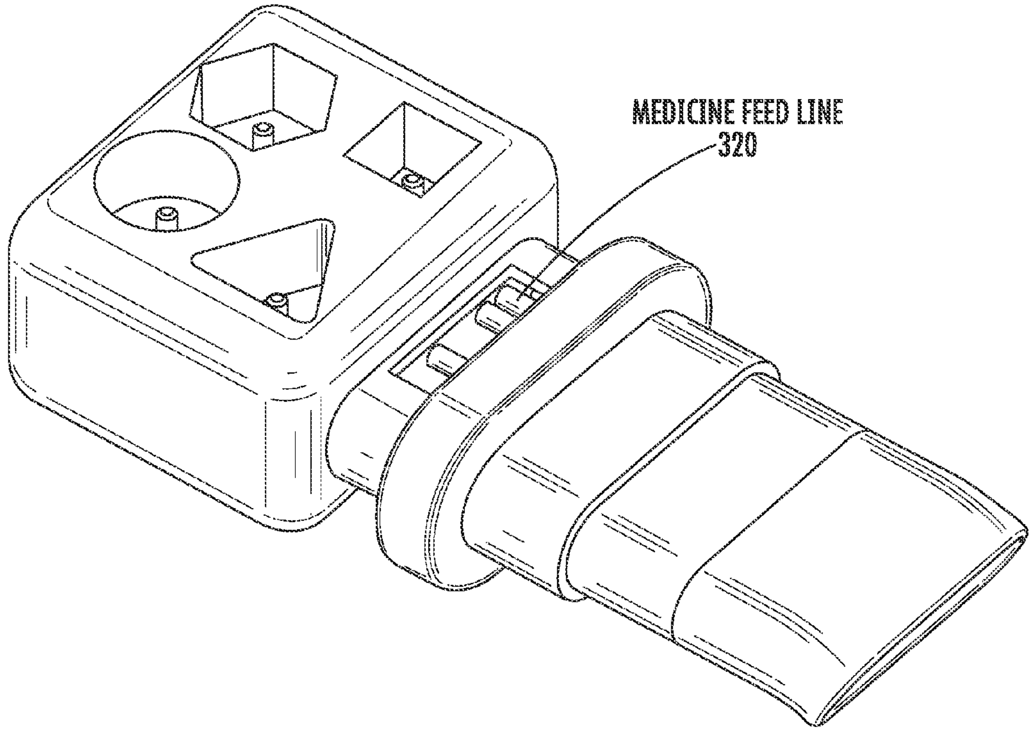
FIG. 15 shows an improved nebulizer in accordance with one aspect of the invention which utilizes four shape-keyed medicine sources with individual medicine feeds to the venturi and mixing chamber.

FIG. 15 shows an improved nebulizer in accordance with one aspect of the invention which uses four shape-keyed medicine sources with individual medicine feeds to the venturi and mixing chamber. It is highly desirable to avoid a situation in which a patient might be given the incorrect medication. To insure the correct medicine is fed to the patient, each of the medicine containers or reservoirs are shaped having a unique shape that is specific for the medication to be administered. This provides a ready mechanism by which medical personal can visually confirm the correct medication being given to the patient. Each medication would be keyed to a particular shape and the shapes would become readily recognizable to medical personal resulting in fewer errors in administration.

It is also the case, that sometimes a plurality of medications would be administered simultaneously. In the case shown in FIG. 15, up to four medications can be administered simultaneously to a patient in the appropriate dosages. As noted above, each medicine container or reservoir can be configured to contain a unit dose of medication, each shaped according to its unique shape. As a result, the correct dosage can be applied to the patient and the dosage is reproducible. Three of the four medication feed lines are shown in FIG. 15, the fourth one not being visible by virtue of the manner of the depiction obscuring the fourth medicine feed line.

Figure 16:
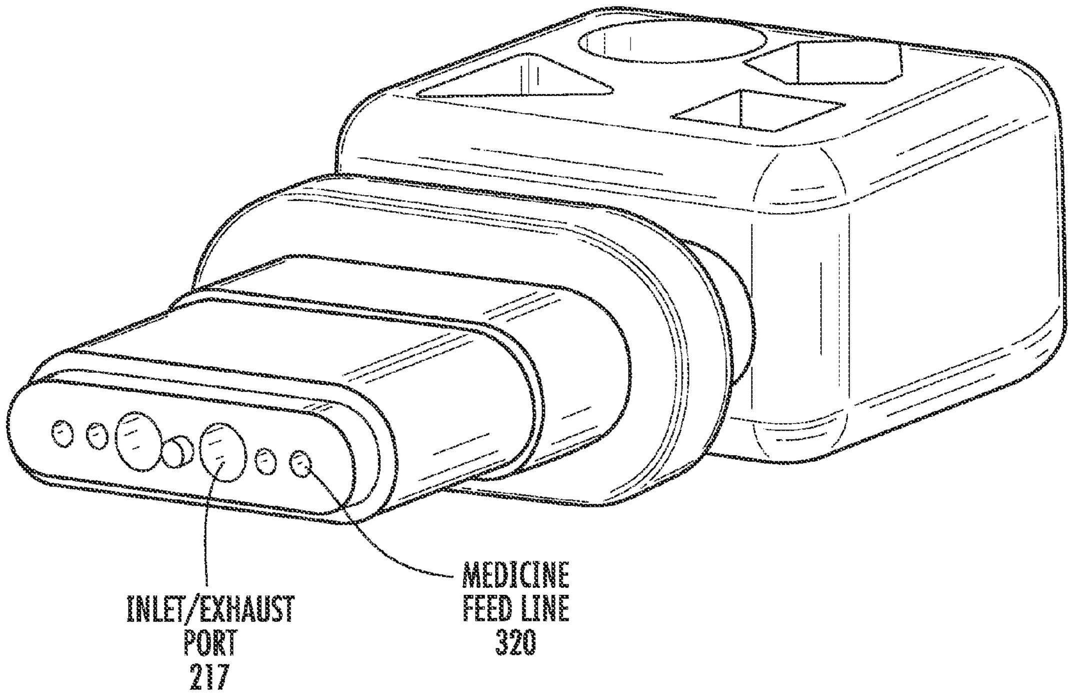
FIG. 16 shows an exemplary fluid/air channel section of the nebulizer of FIG. 15.

FIG. 16 shows an exemplary fluid air channel section of the nebulizer of FIG. 15. In the view shown in FIG. 16, there are four medicine feed lines, one from each of the key-shaped medicine receivers. There are also two larger ports which handle the inlet and exhaust from the patients breathing. In the version shown, the inlet and exhaust passages, the larger holes, feed respective inlet and output ports located behind the rubber mouthpiece shown in FIG. 16. The location of the inlet and outlet exhaust ports can be relocated as convenient without doing violence to the functioning of the nebulizer. For example, it is in some embodiments preferred to have the medicine feed lines located closer to the center line of the longitudinal axis of the nebulizer and have the air inlet/exhaust ports be located on either side of the four medicine feed lines. The latter configuration would be more appropriate where the air inlet/exhaust valves 217 are located on the side of the nebulizer, as shown, for example in FIG. 5, whereas the configuration shown in FIG. 16 might be preferable when the air inlet/exhaust ports are shown on the top of the fluid air channel section 230 as shown in FIG. 8.

Figure 17:
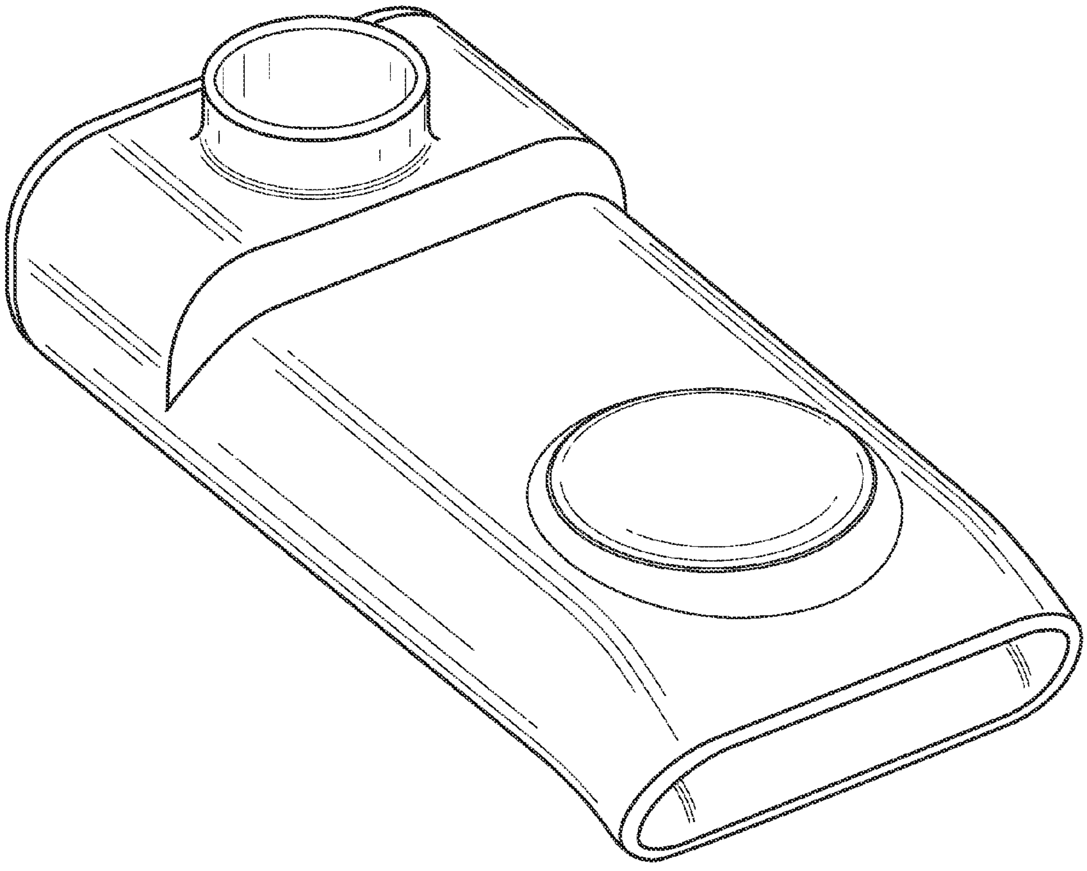
FIG. 17 is a perspective view of an alternative embodiment of a nebulizer in accordance with one aspect of the invention.

FIG. 17 is a perspective view of an alternative embodiment of a nebulizer in accordance with one aspect of the invention. In this view, in the upper left hand portion of the image is a medicine port for receiving a reservoir of medicine for utilization with the inhaler. At the proximal end the circular area shown indicates the location of the rainfall chamber as described more hereinafter. At the distal end, beyond the medicine port, but not shown in this view is an air intake for an air line feeding the venturi inside the nebulization rainfall chamber. The medicine for nebulizer can be filled directly into the reservoir or the nebulizer can come preloaded with the medicine.

Figure 18:
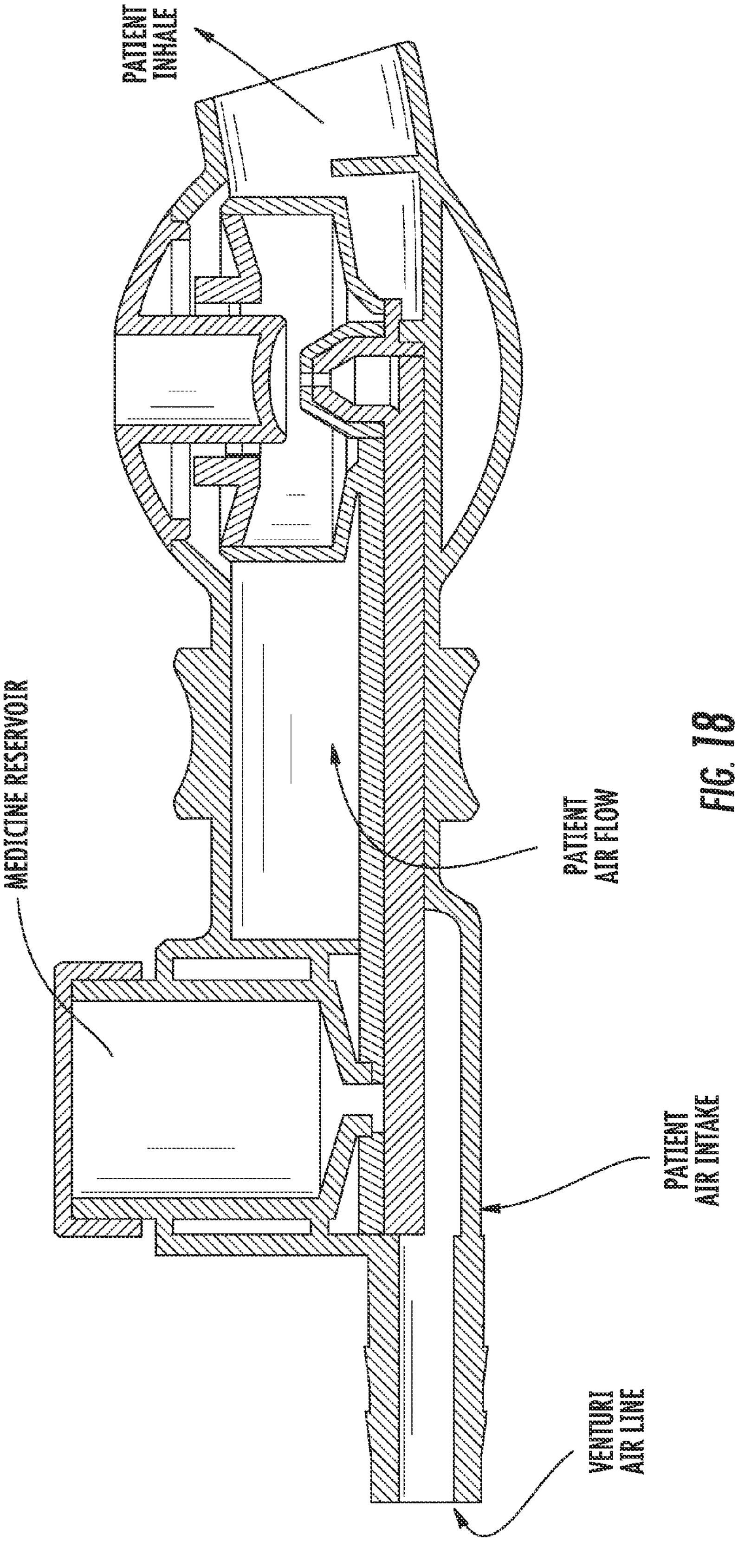
FIG. 18 is a side sectional view of the alternative embodiment of FIG. 17.

FIG. 18 is a side sectional view of the alternative embodiment of FIG. 17. In FIG. 18 the venturi air line is shown at the left end of the illustration. On either side of the venturi air line is a patient air intake port which allows air to be taken in at that port and fed through the body of the nebulizer as shown with the arrow indicating patient air flow direction. The medicine reservoir is shown as well as the patient inhale port for a patient to receive the medication. A cap covers the medicine reservoir. The cap can be screwed on, snapped on or otherwise locked on. The cap can be constructed so medicine can be injected into the reservoir through the cap.

Figure 19:
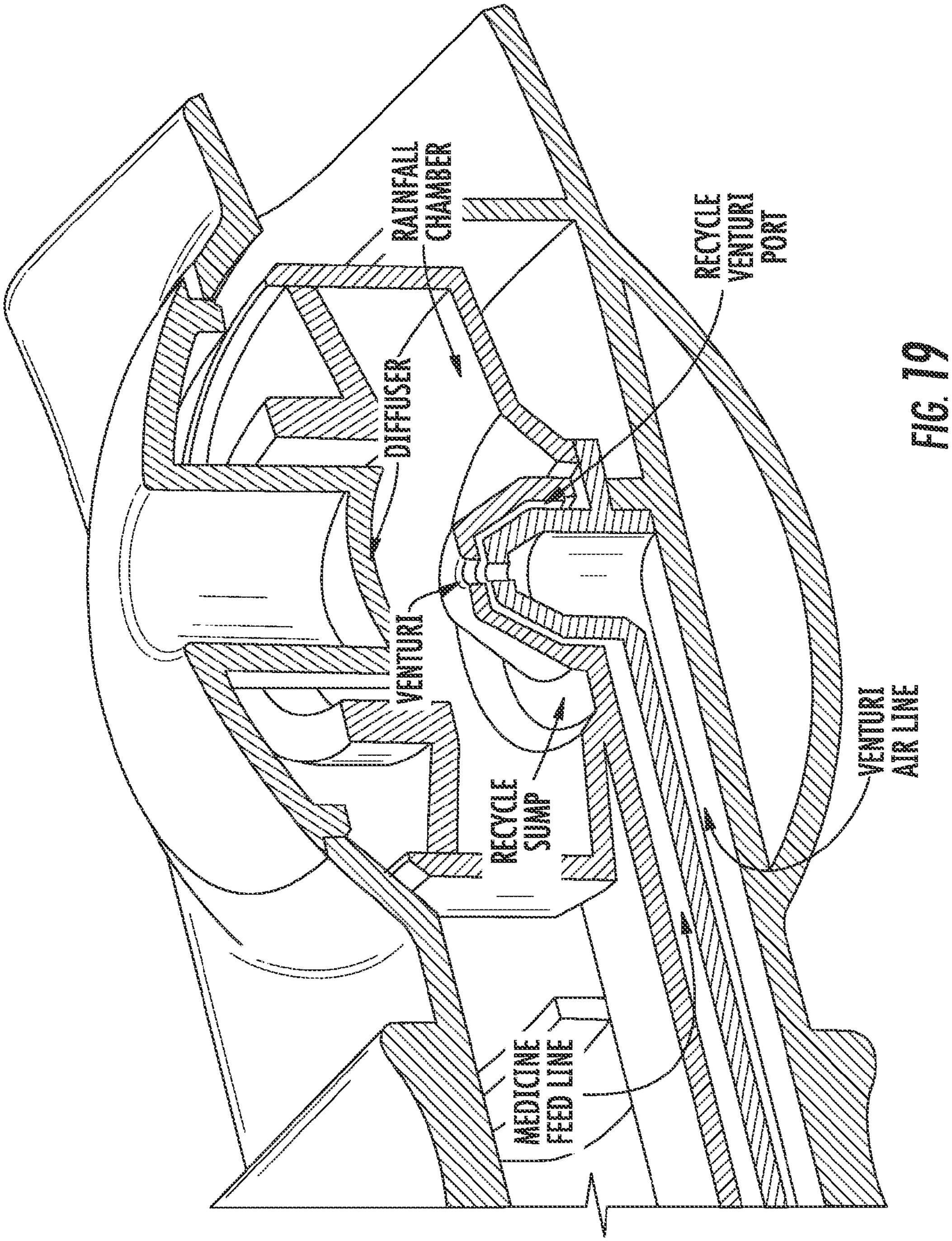
FIG. 19 is a side sectional view of the end of the nebulizer of FIG. 17 that engages the patient's mouth.

FIG. 19 is a side sectional view of the end of the nebulizer that engages the patient's mouth in accordance with one aspect of the invention, showing in more detail the rainfall chamber and the venturi and medicine feed lines. In FIG. 19, one can see the venturi nozzle in approximately the center of the illustration. Right beneath the venturi nozzle is a chamber which is fed by a venturi air line, indicated at the lower portion of the figure to the left of the venturi chamber. Parallel to the venturi airline and located somewhat displaced above the venturi air line is the medicine feed line. Medicine from the reservoir flows through the medicine feed line and through a relatively small opening just prior to the venturi in order to dispense medication into the air flow of the venturi. The venturi effect causes a reduction in pressure which causes the medicine to flow from the reservoir through the medicine feed line and into the venturi space where it is mixed with the air in traditional venturi fashion. The medicine that is nebulized by action of the venturi is expelled from the venturi port in an upward direction toward the diffuser. The diffuser in this case, is shown as textured. It is not necessary that it be textured but texturing may facilitate the break up of the droplets from the venturi into smaller sizes. As the droplets from the venturi bounce off the diffuser and break up, the sizes may not be totally uniform. The air pressure, the feed rate, the velocity with which droplets impact the diffuser and other well known factors can facilitate production of droplets of desired sizes. In fact, droplets can be generated utilizing this arrangement in sizes less than 0.1 microns. Nevertheless, larger droplets may coalesce as they diffuse throughout the rainfall chamber space. As droplets coalesce, they become larger and fall toward the bottom of the chamber where medication that is not utilized is gathered in a recycle sump. Medication found in the recycle sump, is recycled through the recycle venturi port to the proximity with the venturi intake to be reutilized. In this manner, very little medication is wasted and the amount of medication delivered to the patient can be tightly controlled.

When the patient places his mouth on the patient inhale port to the upper right of the image shown in FIG. 19, air from the patient inhale air path will circulate over the rainfall chamber and around the diffuser causing the extraction of droplets from the rainfall chamber for delivery to the patient. Note that the patient inhale air path may go not only over the rainfall chamber but around it to either side with the actual sizing depending upon the need for the amount of air flow to be delivered to the patient during administration of medication.

Returning again to Table 8 of the Respiratory Care article, discussed above, one can see that the invention has many of the characteristics of an ideal aerosol inhaler system as described there.

Dose reliability and reproducibility is enhanced by using unit dose medicine containers. High lung-deposition efficiency is vastly improved over the prior art because the venturi is located near or preferably inside the oral cavity. Very fine particles can be produced in accordance with the invention. The simplicity of use is enhanced by the use of a portable pressurized gas container and value actuation mechanism. The short treatment time is enhanced because the assembly of a seven-piece kit is not required. All that is required is that the medication be inserted into the medicine receiver and the actuator valve for the pressurized gas container is activated to deliver the medication. The nebulizer in accordance with the invention is a smaller size and easier to carry than the seven piece kit. The nebulizer of the invention has multiple dose capabilities, depending on the size of the medicine reservoir. The nebulizer of the invention is resistant to bacterial contamination, because the medication vials do not need to be opened and poured into an open cup as in the prior art. Nevertheless, it is possible to configure the nebulizer of the invention to utilize a cup that can be opened and to pour the medication into the cup as has been done in the past by simply making the medication reservoir with a screw off or pressure fit lid which will allow the medication to be put into the cup as it has been done in the past with the seven piece plastic kit. The nebulizer of the invention is durable and cost effective. Much less of the medication is released to the ambient air by virtue of the positioning of the venturi well within the oral cavity.

Thus, a much improved nebulizer has been disclosed which overcomes the problems of the prior art.

While various embodiments of the present invention have been illustrated herein in detail, it should be apparent that modifications and adaptations to those embodiments may occur to those skilled in the art without departing from the scope of the present invention as set forth in the following claims.

The invention claimed is:

1. A nebulizer comprising:

a main body having an air line and medicine line and a patient receiving end configured to be received within the oral cavity of a patient;

a rainfall chamber formed within the main body;

a venturi nozzle positioned within the rainfall chamber and at a location within the main body adjacent the patient receiving end such that the venturi nozzle is located within the oral cavity or adjacent thereto at the lips of the patient when in use, and said venturi nozzle is connected to the air line and configured to nebulize the medicine and expel droplets outward from the venturi nozzle into the rainfall chamber; and a diffuser positioned within the rainfall chamber upon which the medicine that is nebulized impacts and configured to break up droplets expelled from the venturi nozzle into smaller sizes.

2. The nebulizer of claim 1 wherein the main body includes at least one medicine receiver for receiving medicine.

3. The nebulizer of claim 2 in which the medicine receiver receives a reservoir containing a unit dose of medicine.

4. The nebulizer of claim 3 in which the unit dose is a standardized dose.

5. The nebulizer of claim 2 in which the medicine receiver has a cap.

6. The nebulizer or claim 5 in which the cap screws onto the medicine receiver.

7. The nebulizer of claim 5 in which the cap snaps onto the medicine receiver.

8. The nebulizer of claim 5 in which the cap permits medicine to be injected into the medicine receiver.

9. The nebulizer of claim 2 in which the medicine receiver is filled with medicine.

10. The nebulizer of claim 1 in which the venturi nozzle is provided with a source of gas from the air line.

11. The nebulizer of claim 1 in which the rainfall chamber contains a sump communicating with the venturi for collecting medication not delivered to the patient and for recycling that medication for delivery to the patient.

12. A nebulizer comprising:

a main body having an air line and a medicine line and a patient receiving end configured to be received within the oral cavity of a patient;

an annular configured rainfall chamber formed within the main body;

an upwardly extending venturi nozzle positioned within the central portion of the rainfall chamber and at a location within the main body adjacent the patient receiving end such that the venturi nozzle is located within the oral cavity or adjacent thereto at the lips of the patient when in use, and said venturi nozzle is connected to the air line and configured to nebulize the medicine and expel droplets upward from the venturi nozzle into the rainfall chamber; and a diffuser positioned within the rainfall chamber over the venturi nozzle upon which the medicine that is nebulized impacts and configured to break up droplets expelled from the venturi nozzle into smaller sizes and fall downward throughout the rainfall chamber.

13. The nebulizer of claim 12 in which the rainfall chamber contains a sump communicating with the venturi for collecting medication not delivered to the patient and for recycling that medication for delivery to the patient.

14. A method of administering a medicine to a patient, comprising receiving medicine within a medicine line positioned within a main body having a patient receiving end configured to be received within the oral cavity of a patient, the main body comprising a rainfall chamber formed within the main body and a venturi nozzle positioned within the rainfall chamber and at a location within the main body adjacent the patient receiving end such that the venturi nozzle is located within the oral cavity or adjacent thereto at the lips of a patient when in use;

receiving air within an air line connected to the venturi nozzle and nebulizing the medicine and expelling droplets upward from the venturi nozzle into the rainfall chamber; and breaking up the expelled droplets into smaller droplets when expelled from the venturi nozzle by impacting the droplets as they are expelled from the venturi nozzle onto a diffuser positioned within the rainfall chamber over the nozzle assembly.

15. The method of claim 14 in which the rainfall chamber contains a sump communicating with the venturi for collecting medication not delivered to the patient and for recycling that medication for delivery to the patient.

* * * * *